United States Patent [19]

Cox et al.

[11] Patent Number: 4,659,564

[45] Date of Patent: Apr. 21, 1987

[54] SKIN TREATMENT PRODUCT

[75] Inventors: Ian R. Cox; Zia Haq, both of Merseyside, England

[73] Assignee: Lever Brothers Company, New York, N.Y.

[21] Appl. No.: 703,775

[22] Filed: Feb. 21, 1985

[30] Foreign Application Priority Data

Feb. 24, 1984 [GB] United Kingdom ............... 8404844

[51] Int. Cl.$^4$ ..................... A61K 7/00; A61K 7/32; A61K 7/34; A61K 7/38
[52] U.S. Cl. ........................ 424/65; 424/DIG. 5; 424/47; 424/66; 424/67; 424/68
[58] Field of Search ................. 424/65, 66, 67, 68; 260/287

[56] References Cited

U.S. PATENT DOCUMENTS

| | | | |
|---|---|---|---|
| Re. 27,444 | 7/1972 | Will | 521/63 |
| 3,121,071 | 2/1964 | Sheetz et al. | 526/287 |
| 3,255,127 | 6/1966 | von Bonin | 521/64 |
| 3,256,219 | 6/1966 | Will | 521/63 |
| 3,328,367 | 6/1967 | Rees | 526/287 |
| 3,513,120 | 5/1970 | Pohlemann et al. | 526/287 |
| 3,734,867 | 5/1973 | Will | 521/63 |
| 3,763,056 | 6/1973 | Will | 521/64 |
| 3,937,802 | 2/1976 | Fujimoto et al. | 526/287 |
| 3,988,508 | 10/1976 | Lissant | 526/344 |
| 4,039,489 | 8/1977 | Fletcher | 521/63 |
| 4,460,570 | 7/1984 | Strasilla et al. | 526/287 |
| 4,460,758 | 7/1984 | Peiffer et al. | 526/287 |
| 4,530,986 | 7/1985 | Weiss et al. | 526/287 |
| 4,536,521 | 8/1985 | Haq | 521/146 |

FOREIGN PATENT DOCUMENTS

| | | | |
|---|---|---|---|
| 24175 | 2/1981 | European Pat. Off. | 424/68 |
| 24176 | 2/1981 | European Pat. Off. | 424/67 |
| 60138 | 9/1982 | European Pat. Off. | 424/78 |
| 105634 | 4/1984 | European Pat. Off. | 424/78 |
| 1116800 | 6/1967 | United Kingdom | 524/458 |
| 1485373 | 9/1977 | United Kingdom | 424/68 |
| 1501862 | 2/1978 | United Kingdom | 424/68 |
| 2033730A | 3/1979 | United Kingdom | 424/65 |
| 2067404B | 9/1983 | United Kingdom | 424/68 |

*Primary Examiner*—Dale R. Ore
*Attorney, Agent, or Firm*—Gerard J. McGowan, Jr.; James J. Farrell

[57] ABSTRACT

Skin treatment products especially for absorbing axillary perspiration are described containing certain absorbent polymeric materials having good absorbency for aqueous solutions containing ionic species. The polymeric materials are made by a process which involves the polymerization of a high internal phase emulsion containing 75% to 99% water as the internal phase.

9 Claims, No Drawings

SKIN TREATMENT PRODUCT

This invention relates to skin treatment products. More particularly the invention is concerned with products applied to the axillae in order to mitigate the problem of underarm wetness that is caused by excessive perspiration.

It has been known for many years to mitigate the above problem by the application of compounds that inhibit the production of perspiration, i.e. they reduce the amount of sweat actually produced; these compounds are called antiperspirants. The most commonly employed antiperspirant is aluminium chlorhydrate.

It has also more recently been proposed in GB-PS No. 1 485 373 A and GB-PS 1 501 862 A, both to Unilever, to mitigate the wetness problem by applying particulate polymeric materials that will absorb the secreted perspiration. In each patent it is disclosed that as an optional ingredient, there may also be included in the respective composition, a perspiration depressant such as aluminium chlorhydrate.

The main requirements to be met in employing water-absorbent materials is that they should be able to rapidly absorb sufficient quantities of perspiration, whilst remaining dry to the touch, and provide this effectiveness over a substantial period of time. This they are able to do because between the occasions of the secretion of perspiration the polymeric materials can at least partially dry out (because they absorb reversibly) so that they are able to absorb the perspiration produced at the next sweating cycle. However, it is also a requirement that such absorbent materials perform satisfactorily when used in conjunction with a deodorant compound, the latter being employed in order to prevent the secreted perspiration giving rise to objectionable odour. Such concurrent use with a deodorant compound is referred to in UK Patent No. 2 003 730 A (Unilever). Among the deodorant active compounds that have been suggested are the astringent aluminium-containing compounds which generally also have an antiperspirant action. However, such compounds in aqueous media can chemically react with many absorbent materials and have the adverse effect of reducing the absorptive capacity of the absorbent to an unacceptably low level and, no doubt, the deodorant and antiperspirant activity of the aluminium-containing compounds. This interaction is referred to in European Patent Application No. 80 302726.7 (Publication No. 24175; also in the name of Unilever) where it is proposed to employ in skin treatment compositions containing water-absorbent materials various magnesium and/or lanthanum-containing deodorant compounds which have a high degree of compatibility with water-absorbent polymeric materials. Interaction of an astringent compound with an absorbent material reduces its sweat absorbency capacity. Consequently, in order to optimise the absorbency effect of the water-absorber one should generally avoid the concurrent use of an astringent aluminium compound.

Finally there must also be mentioned the fact that the absorbent materials in the patents referred to have a substantially reduced absorbency for sweat than they do for water. The ionic species present in sweat cause a considerable loss of absorbent power of these absorbers. It is common practice for manufacturer's brochures on absorbers to quote as well as water absorbency the absorbency of a solution of sodium chloride and such a degree of absorbency more realistically indicates the potential absorbency of an absorber for sweat.

It is an object of the invention to provide a skin treatment product which is highly effective in controlling underarm wetness during the secretion of perspiration. In particular it is an object of the invention to provide a skin treatment product comprising an absorbent material having a high absorbency for aqueous media containing ionic species.

According to the invention there is provided a skin treatment product for absorbing axillary perspiration comprising a particulate absorbent polymeric material in combination with a powder, liquid or gel carrier medium, characterised in that the polymeric material is a highly porous, crosslinked polymeric material comprising units of the formula

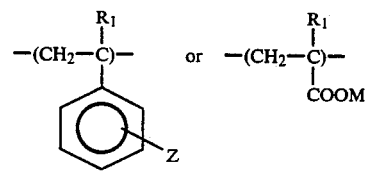

where
$R_1$ is hydrogen or methyl
Z comprises one or more of the following substituents
(a) $-SO_3H$
(b) $-SO_3M$
(c) $-CH_2N^+R_2R_3R_4An^-$
(d) $-CH_2N^+R_2R_3HAn^{31}$

(f) $-CH_2O(CH_2CH_2O)_qH$
(g) $-CH_2SO_3H$
(h) $-CH_2SO_3M$
(i) $-CH_2OSO_3M$
(j) $-COOM$ $R_2$, $R_3$ and $R_4$, which may be the same or different, are alkyl, hydroxyalkyl, cycloalkyl or aryl or $R_2$ and $R_3$ form part of a ring, and where for substituent (c) the total of the carbon atoms for the groups $R_2+R_3+R_4$ is less than 10 and for each of substituents (d) and (e) the total of the carbon atoms for the groups $R_2+R_3$ is less than 8, is an alkali metal, ammonium or substituted ammonium counterion, An is an anion derived from an inorganic acid or from an organic acid containing less than 8 carbon atoms, and q has a value of 2 to 50, the porous structure of the polymeric material comprising continuously interconnected cavities or chambers resulting from the polymerisation of a high internal phase emulsion in which the internal phase is constituted by water in an amount of 75–99% by weight of the emulsion and the external phase by monomer and crosslinking agent.

The above defined functionalised polymers used in products of the invention may be prepared indirectly by chemical modification of a preformed porous polymer block which may, if required, carry a reactive group such as a chloromethyl group or ester functionality, which porous polymer has been prepared from the high-internal phase emulsion polymerisation system. The hydrophilic functional group Z or COOM, respectively is then introduced such as by conversion of the chloromethyl group or ester function. Alternatively, for example, styrene may be polymerised in the high internal phase system and the porous polymer obtained then converted into the porous polymer containing the hydrophilic group Z, either directly by sulphonation or after intermediate chemical modification such as chloromethylation. In a further method the porous polymers may be prepared directly by polymerisation of the high internal phase emulsion in which the emulsified monomer carries the ionic or polar functional group Z, provided that such monomers can form stable polymerisable high internal phase emulsions.

Thus the porous polymeric material employed in the product of the invention may be derived from a cross-linked porous polymeric precursor comprising units of the formula

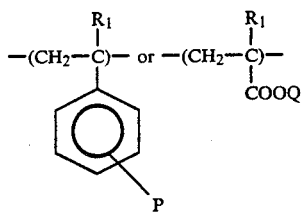

where P is hydrogen or —CH$_2$Cl and Q is an alkyl group containing up to 12 carbon atoms by converting the groups P and Q, respectively, to Z and M by known methods, said porous polymeric precursor being the product from polymerisation of a high internal phase emulsion in which the internal phase is constituted by water in an amount of 75–99% by weight of the emulsion and the external phase by monomer and cross-linking agent.

The polymeric material employed in the skin treatment product of the invention has good absorbency for aqueous fluids containing ionic species. It is a highly porous functionalised polymer having interconnected cavities or chambers which are formed during the polymerisation of the high internal phase emulsion. The internal phase of this emulsion is constituted by water in an amount of 75–99%. As a consequence the polymerisation product has a pore volume of 3 to 99.5% cc/g in its solvent swollen state. The polymeric material desirably comprises a minimum of 30% of the monomer residues carrying the functional groups Z and COOM, respectively. Preferably the degree of substitution or functionalisation of the polymer is at least 50%, most preferably at least 70%. The degree of cross-linking preferably does not exceed 20%, and is preferably 2 to 10%. Other comonomers that can be used to prepare the polymers used in the product of the invention are styrene, α-methylstyrene and other substituted styrenes.

In the polymers described M is preferably sodium, ammonium or a C$_2$–C$_4$ alkyl or hydroxyalkyl-substituted ammonium counterion. The anion An is preferably chloride, sulphate, nitrate, acetate or lactate.

Especially preferred are the sulphonated polymers described and claimed in EP 105 634, the disclosure of which is incorporated herein by reference. These are sulphonated, porous, cross-linked polymeric materials comprising sulphonated hydrocarbon residues prepared by sulphonating a porous, cross-linked polymeric material having a pore volume in the range of from 3.0 to 99.5 cc/g, the sulphonated material having an absorbency for 10% aqueous sodium chloride solution of at least 3 g/g of dry sulphonated material or salt thereof. The hydrocarbon residues may be provided by, for example, styrene or o-vinyl toluene, and the cross-linking can conveniently be achieved using divinyl benzene. At least 15% by weight of the monomers used should be capable of being sulphonated and can conveniently be styrene or styrene equivalent; comonomers can include alkyl acrylates and methacrylates.

The skin treatment product of the invention may take a number of forms. Thus the absorbent polymeric material may be combined with a suitable powder such as talc to form a product for dusting onto the skin, or it may be in the form of a lotion, stick or cream. The product may also comprise a propellant for discharging the active ingredients from an aerosol container onto the skin. These products will be substantially anhydrous, that is they comprise not more than about 5% added water. The water-absorber in particulate form may be suspended in the liquid or gel carrier medium, with the aid of a suitable structuring agent. The methods of formulating the various skin treatment products of the invention will be apparent to those skilled in the art from the above description and from the previous publications referred to. Some preferred forms will now be described in more detail.

The skin treatment product of the invention may be in the form of a lotion, the carrier liquid for such type of product usually being one which is volatile, such as a volatile silicone or other anhydrous liquid suitable for application to the skin, or a mixture of volatile and non-volatile liquids, e.g. a mixture of volatile and non-volatile silicones.

Lotion products are commonly applied to the skin from a roll-on applicator although they may be applied from other applicators, such as a tissue or towellete or porous plastic applicator. The liquid phase also usually comprises an emollient material to provide desirable skin-feel qualities and help to retain the absorbent material on the skin. Especially suitable is isopropyl myristate or other fatty acid esters, such as di-butyl phthalate and di-isopropyl adipate, but other materials well-known to those skilled in the art can also be used, 2or example cetyl alcohol.

To assist in maintaining the absorbent powder in suspension in the lotion a thickening agent is desirably included. Preferably, a hydrophobic clay or colloidal silica is used for this purpose. Hydrophobic clays are available under the trade name Bentone, e.g. Bentone-34 or Bentone-38. Suitable colloidal silicas include Aerosil 200 and Cab-O-Sil M-5 as well as other grades.

Roll-on compositions in accordance with the invention will usually comprise 1–30% polymeric absorbent powder, 0–30% emollient, 0.5 to 10% suspending agent, with the balance consisting essentially of volatile liquid carrier.

Products of the invention in gel form will comprise the usual ingredients to provide a stick base within which the particulate absorbent ingredient is dispersed. Such bases may comprise alcohol thickened to form a gel with sodium stearate or other hard soaps, a long chain alcohol such as stearyl alcohol, stearic monoethanolamide or a volatile silicone solidified with a long chain alcohol as described in U.S. Pat. No. 4,126,679 (Armour-Dial Inc.). The gel preferably also includes materials to improve the skin-feel, such as glycerol. These compositions will usually contain about 1 to 30% by weight of the powdered absorbent material.

The particulate absorbent polymeric material may also be incorporated in a cream base.

The skin treatment composition of the invention may also be in the form of an aerosol, the composition being packaged in an aerosol container together with a gaseous propellant. The aerosol composition may be of the type which a powder is suspended in a liquid vehicle comprising a mixture of a carrier liquid and a liquefied gaseous propellant.

Aerosol compositions of the powder suspension type are well known to those skilled in the art. Conventional carrier liquids and liquefied propellants can be used in aerosol compositions of this invention along with a conventional suspending agent which is frequently included in such products to assist in the suspending of the active powdered ingredient. In particular, the formulation of antiperspirant powder suspension aerosol compositions is well known, and the formulation of the products of this invention can be effected by replacing the powdered antiperspirant active ingredient of such products by a powder of polymeric absorbent material.

The amount of powdered absorbent material present in an aerosol composition of the invention may vary over a wide range but will usually be in the range 0.1 to 15% by weight of the composition. Preferred amounts are from about 0.5% to about 10% by weight of the aerosol composition, particularly 0.5% to 5% by weight. The powder desirably comprises particles less than 100 microns in diameter and preferably is composed essentially of particles having a size of from 10 to 70 microns.

The carrier liquid may for example be a non-volatile non-hygroscopic liquid as suggested in U.S. Pat. No. 3,968,203. Especially useful are carrier liquids which have emollient properties and a number of these are referred to in British Patent Specification No. 1,393,860. Especially preferred are fatty acid esters such as isopropyl myristate and those esters referred to in U.S. Pat. No. 4,045,548 such as dibutyl phthalate and diisopropyl adipate.

Various other carrier liquids for powder suspension aerosols are suggested in U.S. Pat. Nos. 3,974,270, 3,949,066, 3,920,807, 3,833,721 and 3,833,720 and in British Patent Specifications Nos. 1,411,547, 1,369,872, 1,341,748, 1,300,260 and 1,476,117. The use of volatile silicones is described in British Patent Specification No. 1,467,676.

The ratio of the weight of the absorbent powder to the carrier liquid may vary over a wide range, for example from 0.01 to 3 parts, preferably 0.04 to 1 part, of the powder per part by weight of the carrier liquid.

The liquefied propellant can be hydrocarbon, a halogenated hydrocarbon or a mixture thereof. Examples of materials that are suitable for use as propellants are given in the above-mentioned patents and include trichlorofluoromethane, dichlorodifluoromethane, dichlorotetrafluoroethane, propane, butane, 1,1-difluoroethane, 1,1-difluoro-1-chloroethane, dichloromonofluoromethane, methylene chloride, and isobutane, used singly or admixed. Trichlorofluoromethane, dichlorodifluoromethane, dichlorotetrafluoroethane, and isobutane, used singly or admixed, are preferred. Other known propellant ingredients may be present such as carbon dioxide and dimethyl ether.

It is common practice to include in aerosol powder spray compositions a material to assist in the suspending of the powder in the liquid vehicle. The materials prevent compacting of the powder and they may also act as thickening or gelling agents for the liquid vehicle. Especially preferred are hydrophobic clays and colloidal silicas. Hydrophobic clays are available under the trade name Bentone, e.g. Bentone-34 or Bentone-38, and their use as suspending agents is described in a number of patent specifications including U.S. Pat. No. 3,773,683. Suitable colloidal silicas include Aerosil 200 and Cab-O-Sil M-5 as well as other grades.

Further information concerning the formulation of products containing an absorbent polymer is, of course, also given in the specifications already mentioned above which relate to this general topic, viz GB Patent Specifications Nos. 1,485,373, 1,501,862, 2,003,730 and 2,067,404.

The products of the invention also preferably comprise a deodorant agent. The deodorant may be a deodorant composition as defined and as described in GB-PS No. 2,013,493A. Alternatively, the deodorant may be a particulate substance which may or may not also be an antiperspirant. Suitable deodorant agents, not having an antiperspirant effect, are referred to in European, patent applications No. 80 302726.7 (Publication No. 24175), already mentioned above, and No. 80302727.5 (Publication No. 24179). These applications relate particularly to the use as deodorants of the oxides, hydroxides and carbonates of magnesium and lanthanum, and zinc carbonate, respectively, but also refer to various other already known deodorant active materials. Zinc oxide is another suitable deodorant agent. By contrast, zinc phenolsulphonate is an example of a soluble deodorant active compound that may be used in conjunction with the absorbent polymer.

The skin treatment product of the invention may comprise an antiperspirant material such as any of those mentioned in the specifications already referred to.

However, the antiperspirant active material preferably employed in the skin treatment product of this invention is desirably one which is highly active. Antiperspirants falling into this category are special active forms of basic aluminium chloride having a particular distribution of polymeric species in aqueous solution and obtainable by the process of U.S. Pat. No. 4,359,456 (Gosling et al). The forms of basic aluminium chloride which have enhanced activity are those having a Band III Percent Aluminium Value (as determined by the chromatographic procedure described in the patent) of at least 20%.

Other highly active antiperspirants are the aluminium zirconium chlorhydrate complexes. Examples are aluminium zirconium trichlorhydrate, aluminium zirconium tetrachlorohydrate and aluminium zirconium pentachlorohydrate (these are CTFA generic names). These compounds may be combined with glycine to give for example the compounds known under the CTFA generic names aluminium zirconium trichlorohydrex-GLY and aluminium zirconium tetrachlorohydrex-GLY. Methods for preparing aluminium zirconium chlorhydrates are described in a number of patents, for example U.S. Pat. Nos. 4,028,390 (Armour) and 3,792,068 (Procter & Gamble). Suitable aluminium zirconium chlorhydrate powders for use in the skin treatment products of this invention are available from the Reheis Chemical Company under the trade names REZAL 36GP and REZAL 67P (REZAL is a trade mark).

The antiperspirant agent will usually be present in an amount in the range 2 to 50% by weight of the product. It may be present as a powder or in solution in an appropriate solvent or mixture of solvents so selected that undesirable swelling of the absorbent polymer does not occur.

There will now be described the preparation of various polymeric materials suitable for use when in particulate form in the products of the invention.

Preparation of a sulphonate of the type where Z is $-SO_3M$

A polystyrene having a void volume of approximately 97.5% was prepared using the following materials:

| | |
|---|---|
| Styrene | 66.7 ml |
| Divinyl benzene (cross-linking agent) | 6.7 ml |
| Sorbitan monooleate (emulsifier) | 13.3 g |
| Sodium persulphate (initiator) (0.2% solution) | 2000 ml |

The styrene, divinyl benzene and sorbitan monooleate were placed in a 2-liter plastics beaker fitted with a helical stirrer coated with polytetrafluoroethylene. The sodium persulphate was added dropwise using a carefully controlled stirring regime such that a high internal phase "water-in-oil" type emulsion was produced, and the batch was then maintained at 50° C. overnight to polymerise. The solid thus formed was cut out of the beaker, chopped to approximately 1 cm cubes, squeezed to near dryness using a mangle, then dried in a vacuum oven at 60° C. for 48 hours.

100 g of the chopped, dried polystyrene was stirred into 5 liters of concentrated (98%) sulphuric acid preheated to 120° C. The material wetted after 10 minutes and then swelled to absorb all the acid over a period of 2 hours. The mixture was allowed to stand overnight to cool and then filtered through a sheet of 15 g/m² polypropylene/viscose nonwoven fabric, using a 38 cm Buchner funnel, while pressure was applied with a dam of polytetrafluoroethylene. 2.5 liters of acid were collected and disposed of. The pressed sulphonate polymer was added slowly and carefully to 12 liters of deionised water in a large vessel; substantial heat was evolved during this operation. The polymer was then filtered. The crude polymer sulphonic acid thus obtained was washed free of acid and dried.

60 g of the washed, dried, acid sulphonated porous polymer (pore volume 35.5 cc/g, degree of sulphonation greater than 95%, and an ion exchange capacity of 3.8 mg/g) was added to 12 liters of 10% sodium carbonate solution. The wet sodium salt was centrifuged in a cotton bag in a spin drier for 10 minutes, rewet with deionised water and recentrifuged (this was conducted 5 times). When the washings from the polymer were free from carbonate, the polymer was dried at 170° C. for 5 hours. The product contained 8.2–8.8% sodium and had an ion exchange capacity of 3.8 meq/g.

Preparation of a cationic polymer of the type where Z is $-CH_2N^+R_2R_3R_4AN^-$ The preparation of a chloromethyl styrene porous polymer will first be described.

2.5 gm Span 80 (sorbitan mono-oleate) and 1 cm³ commercial divinyl benzene/ethyl vinyl benzene (50:50) are dissolved in 10 cm³ chloromethylstyrene monomer in a polypropylene beaker. To this is added dropwise a solution of 0.75 gm potassium persulphate dissolved in 300 cm³ water while continuously stirring the mixture so that a water-in-oil high internal phase emulsion is formed. After complete addition of the aqueous phase, the beaker is sealed and heated to 60° C. in a water bath to effect polymerisation. After 18 hours, a solid block of wet polymer is obtained which is dried in air at 30 to 40° C. The dried polymer can then be chemically modified directly or may be soxhlet extracted with hexane to remove the emulsifier prior to further chemical treatment.

The preformed chloromethylstyrene porous polymer in a round bottomed flask was vacuum filled with an aqueous solution of trimethylamine (or with an ethanolic solution of other water-insoluble amines) with the amine present at 10 times molar excess. The reactants were heated for 30 minutes under reflux conditions, during which time the polymer shows considerable swelling and additional solvent (water or ethanol) may be required to maintain the polymer under the surface of the liquid. The cationic product was removed from the reaction mixture, washed extensively with water or ethanol and then methanol to remove unreacted tertiary amine. The solids were then allowed to air dry from the methanol saturated state.

The liquid absorption data were as follows:

| | | |
|---|---|---|
| water | 50 | g per g of polymer |
| 10% NaCl | 50.5 | g per g of polymer |
| 20% NaCl | 49.0 | g per g of polymer |

These data were determined by placing approximately 100 mg samples of the polymer in a Petri dish and saturating them with the test fluid. After 10 minutes the excess fluid was withdrawn and the amount of absorbed fluid determined by weight. This method was also used for determining the absorbencies of other polymer types referred to herein.

Preparation of amine salts of the type where Z is $-CH_2N^+R_2R_3H\ An^-$

The preformed chloromethylstyrene porous polymer in a round bottomed flask was vacuum filled with aqueous dimethylamine solution (or an ethanolic solution of other water-insoluble amines) with the amine present in 10 times molar excess. The reactants were heated for up to 10 hours under reflux conditions, during which time the polymer swells. The polymer was isolated and washed thoroughly with solvent to remove excess amine and the amino derivative so obtained treated with acid, such as methanolic HCl, to form the amine salt. The polymer was again washed and dried in air to yield the desired amine salt.

The product obtained absorbed 50.4g of water per gram of polymer and 41.0g of 10% sodium chloride solution per gram of polymer.

Preparation of amine oxide polymers of the type where Z is

These polymers are readily prepared from the amine derivatives obtained as above (prior to salt formation) by vacuum filling the dried polymer with a 30% hydrogen peroxide solution (peroxide present in large excess) and heating the reactants at 60°-70° C. in a water bath for up to 10 hours. The polymer is then isolated, washed with water until peroxide free, then washed with methanol and dried in air.

The polymer for which both $R_2$ and $R_3$ were ethyl groups and for which the level of substitution of the functional amine oxide group was 85% absorbed 55g and 57g of water and 10% NaCl, respectively, per gram of polymer.

Preparation of alkoxylated polymers of the type where Z is $-CH_2O(CH_2CH_2O)_qH$ Chloromethyl styrene polymer is vacuum filled with the anionic form of a polyethylene glycol in excess polyethylene glycol as solvent. In some instances, the glycol itself is too viscous at room temperature to enter the pores of the polymer, even under vacuum, in which case the glycol is heated to reduce its viscosity to a point where the polymer can be vacuum filled. The mixture is treated slowly with a molar excess of sodium hydride at room temperature to form the glycolate anion. When hydrogen evolution has stopped, the mixture is then heated at 90°-100° C. for periods up to 30 hours. Precautions are taken throughout to prevent the entry of moisture into the reaction mixture. The solids are recovered, washed with water until glycol and alkali free, then washed with methanol and dried.

Other processes which can be employed include those in which the polymer is treated with the glycol anion in a suitable inert solvent, especially where the glycol has such a high molecular weight that it is too viscous/solid to enter the polymer pores even under heating/vacuum. Other standard ethoxylation processes, such as the use of ethylene oxide for the ethoxylation of hydroxy or carboxy functionalised polymers, can also be used.

The absorption capacity, particularly with aqueous systems, increases with increasing EO chain length and the elastic rubbery texture of the polymer disappears as the EO chain length is reduced, i.e. the 2EO sample is still elastic but subjectively less so than the other materials.

Absorbency data for some polymers of this type are given below.

| Value of q | Degree of Substitution | Liquid Absorption (g/g) | | |
|---|---|---|---|---|
| | | Water | 10% NaCl | 20% NaCl |
| 8-9 | 90% | 18 | 15.5 | 21.0 |
| 4 | 90% | 8.5 | 10.0 | 7.0 |
| 2 | 90% | 7 | 7.0 | 7.4 |

Preparation of sulphonates of the type where Z is $-CH_2SO_3M$

The dried form of the cationic triethylammonium substituted polymer (degree of substitution 80%) was allowed to swell in water, a large molar excess of sodium sulphite dissolved and the mixture adjusted to pH 9. The reactants were refluxed for extended periods up to 70 hours to give a product with a high level of sulphonation. The polymeric solids were recovered, washed with water, then methanol and dried to give collapsed, brittle polymer particles that were hydrophilic and water-swellable.

The polymer absorbed 40g of water per gram of polymer and 50g of 10% sodium chloride solution per gram of polymer.

Preparation of sulphates of the type where Z is $-CH_2OSO_3M$

The chloromethylstyrene porous polymer is treated with sodium or potassium acetate (10 times molar excess) in dimethylformamide (DMF) as solvent. The mixture is heated at reflux for up to 15 hours, following which the polymer is isolated and washed thoroughly with water to remove the DMF and excess acetate salt. This yields the wet acetoxy derivative which may be dried for characterisation or the wet polymer can be transferred directly into caustic soda solution (50:50 aqueous ethanol) and refluxed for up to 15 hours to hydrolyse the acetate ester. The product is then washed with water until free of alkali, washed with methanol and dried to give the hydroxymethyl polymer. This hydroxymethylstyrene polymer can, in principle, be sulphated by a number of standard techniques, but is preferably sulphated under conditions of low acidity such as with the sulphur trioxide : amine complexes. For example, about 10 times molar excess of commercial pyridine: $SO_3$ complex was dissolved in DMF and the dried hydroxymethyl polymer added. The mixture was heated on a steambath for 35 hours. Work-up and neutralisation of the product followed by washing in water and then methanol yielded the desired sulphate salt.

Preparation of a carboxylated polymer of the type where Z is $-COOM$

The hydroxymethyl polymer, prepared as described above, is vacuum filled with concentrated nitric acid and heated on a steam bath for up to 6 hours, following which the polymer is isolated, washed thoroughly with water until acid free, treated with excess caustic soda solution to form the carboxylate salt, and the polymer then washed with water and methanol and dried to yield the nitrated and carboxylated product. Alternatively, the polymer can be vacuum filled with an aqueous alkaline solution of potassium permanganate and heated on a steam bath for one hour. The polymer is then isolated, washed free of permanganate and treated with acidic sodium metabisulphite solution to remove manganese dioxide. The polymer is further washed with water, treated with caustic soda solution to form the carboxylate salt and subsequently washed with water, methanol and dried to yield the carboxylated product.

A carboxylate salt absorbed 53g of water per gram of polymer and 12.5g of 10% sodium chloride solution per gram of polymer.

Preparation of a polyacrylate

Polyacrylate materials are prepared by hydrolysis of the corresponding acrylate ester. These acrylate ester polymers are prepared in a similar manner to that used for chloromethylstyrene with sorbitan monooleate as emulsifier. The hydrolysis can be achieved by aqueous sulphuric acid of between 50 and 90% concentration. Preferably the hydrolysis is carried out at elevated temperature, e.g. 60° C. Suitable acrylate esters are t-butyl acrylate, butyl acrylate, hexyl acrylate and 2-ethylhexyl acrylate and the corresponding methacrylate esters.

Suitable comonmers such as styrene can also be employed.

Examples of products in accordance with the invention are described below. In these Examples the polymeric absorbent materials employed were the sulphonated polystyrene materials, prepared as described above, in both the acid and sodium salt forms. These materials were ground and sieved to produce powders having the following particle size distributions.

| Size range | Percentage by weight | |
| (Microns) | H+ form | Na+ form |
| --- | --- | --- |
| 0–10 | 37.6 | 29.5 |
| 10–20 | 31.5 | 60.4 |
| 20–30 | 21.6 | 9.5 |
| 30–50 | 6.6 | 1.5 |
| 50–64 | 0.6 | — |
| >64 | — | — |
| Mass median diameter (microns) | 13.4 | 12.95 |

The absorbency of these powders was determined as follows.

30g of the particulate absorbent material are placed in a weighed (centrifugable) sinter tube. The test solution is added dropwise until no further liquid uptake is observed. The sinter tube is reweighed.

| | |
| --- | --- |
| Weight of tube | $= W_1$ |
| Weight of tube + dry absorbent | $= W_2$ |
| Weight if tube + wet absorbent | $= W_3$ |
| Absorbency of absorbent material | $= \dfrac{W_3 - W_2}{W_2 - W_1}$ g/g |

The absorbencies (g/g) of the powders were determined for various test liquids and the data obtained are given below. For comparison purposes corresponding figures are given for a powdered water-insoluble crosslinked sodium carboxymethyl cellulose milled and classified to less than 45 microns (referred to below as X-CMC).

| | Test Liquid | | | | |
| | Deionised Water | 0.1 M Saline | 10% ACH[1] | 10% Rezal 36GP[2] | 10% ZnPS[3] |
| --- | --- | --- | --- | --- | --- |
| Polymer (H+ form) | 33.3 | 34.8 | | | |
| Polymer (Na+ form) | 91.1 | 92.2 | 48.1 | 38.3 | 48.4 |
| X-CMC | 57.4 | 29.8 | 7.3 | 1.5 | 1.5 |

[1] Aluminium chlorhydrate in activated form obtained by the process of U.S. Pat. No. 4,359,456
[2] Aluminium zirconium hydroxychloride glycine complex
[3] Zinc phenolsulphonate In the Examples data are also given for the absorbency of the skin treatment products themselves. The methods of making the measurements will now be described.

The method of determining the absorbency of a skin treatment product which, combined with a propellant, is in aerosol form will first be described.

The procedure was as follows. A test tube was cleaned and weighed to three decimal placed ($W_1$). A ring of a masking material was applied to the test tube so as to leave the lower 5 cms exposed. The tube was fitted to a rubber bung mounted on the vertical drive shaft of a motor and spun at about 100±20 rpm about its longitudinal axis. While the tube was rotating the aerosol composition was sprayed (for about 5 seconds) on to the exposed part of the tube (except the curved base) to obtain an even deposit of about 25 mg dry weight. The motor was stopped, the tube released and the mask immediately removed. The top of the tube was wiped clean and dry if necessary. The deposit was left for one hour to allow the volatile components to evaporate when the tube was reweighed, again to three decimal places ($W_2$).

A filter paper of at least 7 cm diameter was folded into a strip and wrapped as a ring around the tube at the top and fixed with a rubber band or twist of soft wire. The ring of paper was slid down the tube so that its edge did not quite touch the film of the applied product. The purpose of the paper ring was to prevent water running from the top of the tube onto the applied product. The tube was then remounted on the shaft.

The tube was spun and the coated part sprayed with 0.1M sodium chloride to give a good initial moistening. Subsequent spraying after a short soak-in period was done with a slow delivery spray gun. The process took several minutes, and the saline solution was applied as a fine mist, at intervals, the addition becoming slower as fluid began to collect on the bottom of the tube. The object was to add just enough water to cause one drop to fall, but not more than that.

As soon as one drop fell, the motor was stopped, the tube released and the paper ring removed. The top of the tube was wiped and the tube weighed, again to three decimal places ($W_3$), without delay.

The product absorbency is calculated from the following expression:

$$\text{Product Absorbency} = \dfrac{W_3 - W_2 - K}{W_2 - W_1} \text{ g/g}$$

The factor K is related to the experimental set-up used in these test procedures and should be determined separately for each new set-up. In Applicant's experiments K had the value of 0.090. The determination of K involved completing six trials measuring saline uptake (y) as a function of applied amount of product (x) for a wide range of applied levels. The data conform to $y = mx + K$.

The above description of the measurement of product absorbency has been described for the case where the product tested was in the form of an aerosol. For products in the form of a lotion, e.g. a roll-on product, the product was applied to the test tube using a soft brush. After leaving the product to dry to constant weight, e.g. for 1 hour, the same procedure as described above was adopted. For products in the form of sticks, the end of the stick was pressed against the end of the test tube while rotating the tube slowly until the lower part of the tube was covered with a film of the product. After drying for one hour at ambient temperature, the saline absorbency was determined as described above.

The following Examples illustrate skin treatment products of the invention. Precentages are by weight.

EXAMPLE I

The following aerosol product was formulated

| Compound | % |
| --- | --- |
| H+ form of sulphonated polymer | 2.0 |

-continued

| Compound | % |
|---|---|
| ACH[1] | 4.0 |
| Isopropyl myristate | 4.0 |
| Bentone 38[2] | 0.5 |
| Perfume | 0.4 |
| Laurex CS[3] | 0.5 |
| CAP 40[4] | 29.0 |
| Propellants 11 & 12 (1:1) to | 100.0 |

[1]Aluminium chlorhydrate in activated form obtained by the process of U.S. Pat. No. 4,359,456
[2]a quaternary ammonium hectorite clay
[3]a commercial mixture of cetostearyl alcohols supplied by Albright & Wilson
[4]a hydrocarbon blend consisting mainly of propane and butane and having a vapour pressure of about 3.2 bars.

The product had an absorbency for 0.1M saline of 3.0 g/g and the polymer had an intrinsic absorbency for 0.1M saline of 17.1 g/g.

The intrinsic absorbency (IA) of the polymeric absorbent is the value for the absorbency of the absorbent in the applied product. The intrinsic absorbency is calculated from the value for the product absorbency (PA) and the proportion of the absorbent in the applied product after volatilisation of any volatile components of the product.

$$IA = PA \times \frac{\text{Weight of product after volatisation of any volatiles}}{\text{Weight of absorbent}}$$

Thus the intrinsic absorbency after initial wetting of the absorbent of Example I is:

$$3.0 \times \frac{11.4}{2.0} = 17.1 \text{ g/g}$$

The value for the intrinsic absorbency as compared with the absorbency for the absorbent itself as determined by Test Procedure II is indicative of the effect that the other product components have on the absorbency of the absorbent.

From the product absorbency, the weight of sweat absorbed by the applied product may readily be calculated and is given by:

Product absorbency (g/g)×Non-volatile deposit (mg)

For a typical aerosol application giving a product deposit of 300 mg, the formulation in Example I would give 3.0×300=900 mg 0.1M saline absorbency.

EXAMPLES II and III

The following aerosol compositions were prepared.

| Component | % Example II | Example III |
|---|---|---|
| Na+ form of sulphonated polymer | 1.5 | 1.5 |
| ACH | 4.0 | 4.0 |
| Bentone 38 | 0.5 | 0.5 |
| Isopropyl myristate | 4.0 | — |
| Volatile Silicone VS 7207[1] | — | 4.0 |
| Perfume | 0.4 | 0.4 |
| Laurex CS | 0.5 | 0.5 |
| CAP 40 | 29.0 | 29.0 |
| Propellants 11/12 (1:1) | to 100.0 | to 100.0 |

[1]a cyclic polydimethylsiloxane mainly tetramer.

The 0.1 M saline intrinsic absorbencies (g/g) of the products of Examples II and III are 16.0 and 17.4, respectively.

EXAMPLES IV and V

The following aerosol products were made.

| Component | % Example IV | Example V |
|---|---|---|
| Na+ form of sulphonated polymer | 1.0 | 1.0 |
| Isopropyl myristate | 3.0 | — |
| Volatile silicone VS 7207 | — | 3.0 |
| Bentone 38 | 0.3 | 0.3 |
| Industrial Methylated Spirit | 3.0 | 3.0 |
| Perfume | 0.4 | 0.4 |
| Laurex CS | 0.5 | 0.5 |
| Basic Zinc carbonate | 1.5 | 1.5 |
| Propellants 11/12 (1:1) | to 100.0 | to 100.0 |

The 0.1M saline intrinsic absorbencies (g/g) of the products of Examples IV and V are 29.9 and 39.3, respectively.

EXAMPLES VI-14 VIII

The following roll-on products were made.

| Component | % VI | VII | VIII |
|---|---|---|---|
| Na+ form of sulphonated polymer | 20.0 | 10.0 | 10.0 |
| ACH | 20.0 | 25.0 | 25.0 |
| Bentone 38 | 2.0 | 3.5 | 3.5 |
| Isopropyl myristate | 56.0 | — | 10.0 |
| Volatile silicone VS 7207 | — | 59.0 | 49.0 |
| Perfume | 2.0 | 2.5 | 2.5 |

The 0.1 M saline intrinsic absorbencies (g/g) of the products of examples VI, VII and VIII are 17.0, 16.6 and 14.3, respectively.

EXAMPLE IX

The following stick product was made.

| Component | % |
|---|---|
| Na+ salt of sulphonated polymer | 16.0 |
| ACH | 16.0 |
| Castorwax MP 80[1] | 4.0 |
| Syncrowax[2] | 3.0 |
| Volatile silicone VS 7158[3] | 40.0 |
| Talc | 2.0 |
| Perfume | 1.0 |
| Stearyl alcohol | 18.0 |

[1]Hydrogenated castor oil (glyceryl tri-12-hydroxy stearate)
[2]Glyceryl tribehenate
[3]Cyclic dimethyl siloxane (mainly pentamer)

The 0.1M saline intrinsic absorbency (g/g) of the Product of Example IX was 13.6.

EXAMPLES X to XIII

| Component | % Example: X | XI | XII | XIII |
|---|---|---|---|---|
| Na+ salt of sulphonated polymer | 1.0 | 1.0 | 1.0 | 1.0 |
| Bentone 38 | 0.3 | 0.3 | 0.3 | 0.3 |
| Isopropyl myristate | — | 2.0 | — | 2.0 |
| Volatile silicone VS 7207 | 2.0 | — | 2.0 | — |
| Deodorant composition[1] | 0.3 | 0.3 | 0.3 | 0.3 |

| Component | % Example: | | | |
|---|---|---|---|---|
| | X | XI | XII | XIII |
| CAP 40 | to 100 | to 100 | — | — |
| Propellant 11/12 (1:1) | — | — | to 100 | to 100 |

[1] as described in GB-PS 2 013 493A.

While in the above Examples the absorbent polymers employed have sulphonate frictional groups (i.e. the substituent group Z is —SO$_3$H or —SO$_3$Na), these polymers may be substituted by the polymers containing other functional substituents as described herein.

We claim:

1. A skin treatment product for absorbing axillary perspiration comprising an effective amount of a particulate absorbent polymeric material in combination with a powder, liquid or gel carrier medium, characterised in that the polymeric material is a highly porous, cross-linked polymeric material comprising units of the formula

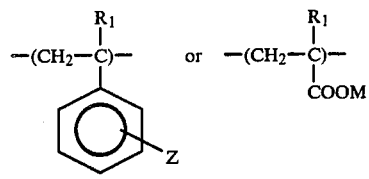

where
$R_1$ is hydrogen or methyl
Z comprises one or more of the following substituents
 (a) —SO$_3$H
 (b) —SO$_3$M
 (c) —CH$_2$N$^+$R$_2$R$_3$R$_4$An$^-$
 (d) —CH$_2$N$^+$R$_2$R$_3$HAn$^-$ (e) 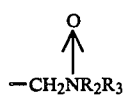

(f) —CH$_2$O(CH$_2$CH$_2$O)$_q$H
 (g) —CH$_2$SO$_3$H
 (h) —CH$_2$SO$_3$M
 (i) —CH$_2$OSO$_3$M
 (j) —COOM $R_2$, $R_3$ and $R_4$, which may be the same or different, are alkyl, hydroxyalkyl, cycloalkyl or aryl or $R_2$ and $R_3$ form part of a ring, and where for substituent (c) the total of the carbon atoms for the groups $R_2+R_3+R_4$ is less than 10 and for each of substituents (d) and (e) the total of the carbon atoms for the groups $R_2+R_3$ is less than 8, M is an alkali metal, ammonium or substituted ammonium ion, An is an anion derived from an inorganic acid or from an organic acid containing less than 8 carbon atoms, and q has a value of 2 to 50, the porous structure of the polymeric material comprising continuously interconnected cavities or chambers resulting from the polymerisation of a high internal phase emulsion in which the internal phase is constituted by water in an amount of 75–99% by weight of the emulsion and the external phase by monomer and cross-linking agent.

2. A product as claimed in claim 1, wherein the porous polymeric material is derived from a cross-linked porous polymeric precursor comprising units of the formula

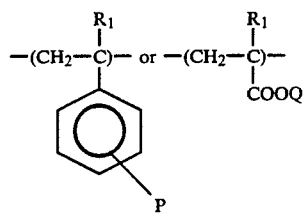

where P is hydrogen or —CH$_2$Cl and Q is an alkyl group containing up to 12 carbon atoms by converting the groups P and Q, respectively, to Z and M by known methods, said porous polymeric precursor being the product from polymerisation of a high internal phase emulsion in which the internal phase is constituted by water in an amount of 75–99% by weight of the emulsion and the external phase by monomer and cross-linking agent.

3. A product as claimed in claim 1 in which the polymer is a sulphonated polystyrene wherein $R_1$ is hydrogen and Z is —SO$_3$H.

4. A product as claimed in claim 1 in which the polymer is a sulphonated polystyrene wherein $R_1$ is hydrogen and Z is —SO$_3$M.

5. A product as claimed in claim 4 wherein Z is —SO$_3$Na.

6. A product as claimed in claim 1 in the form of an aerosol product in which the particulate polymer is suspended in a liquid vehicle comprising a propellant.

7. A product as claimed in claim 1 in which the product is in the form of a lotion for dispensing from a roll-on applicator, the particulate polymeric absorbent being dispersed in a liquid vehicle.

8. A product as claimed in claim 1 wherein the product also comprises a particulate active material.

9. The product as claimed in claim 1 further comprising a deodorant agent.

* * * * *